United States Patent
Trabelsi

(10) Patent No.: US 9,023,334 B2
(45) Date of Patent: May 5, 2015

(54) COMPOSITION FOR MAKING UP THE LIPS

(75) Inventor: Vanessa Trabelsi, Villemomble (FR)

(73) Assignee: Chanel Parfums Beaute, Neuilly sur Seine (FR)

( * ) Notice: Subject to any disclaimer, the term of this patent is extended or adjusted under 35 U.S.C. 154(b) by 648 days.

(21) Appl. No.: 12/524,108

(22) PCT Filed: Jan. 23, 2008

(86) PCT No.: PCT/EP2008/050780
§ 371 (c)(1),
(2), (4) Date: Jul. 22, 2009

(87) PCT Pub. No.: WO2008/090187
PCT Pub. Date: Jul. 31, 2008

(65) Prior Publication Data
US 2010/0034767 A1    Feb. 11, 2010

(30) Foreign Application Priority Data
Jan. 23, 2007  (FR) ..................................... 07 00457

(51) Int. Cl.
| | | |
|---|---|---|
| *A61K 31/74* | (2006.01) | |
| *A61Q 90/00* | (2009.01) | |
| *A61K 8/06* | (2006.01) | |
| *A61K 8/31* | (2006.01) | |
| *A61K 8/81* | (2006.01) | |
| *A61K 8/90* | (2006.01) | |
| *A61Q 1/02* | (2006.01) | |
| *A61Q 1/04* | (2006.01) | |
| *A61Q 1/10* | (2006.01) | |

(52) U.S. Cl.
CPC . *A61K 8/064* (2013.01); *A61K 8/31* (2013.01); *A61K 8/8111* (2013.01); *A61K 8/8117* (2013.01); *A61K 8/90* (2013.01); *A61K 2800/594* (2013.01); *A61Q 1/02* (2013.01); *A61Q 1/04* (2013.01); *A61Q 1/10* (2013.01)

(58) Field of Classification Search
CPC ... A61K 2800/594; A61K 8/064; A61K 8/31; A61K 8/8111; A61K 8/8117; A61K 8/90
See application file for complete search history.

(56) References Cited

U.S. PATENT DOCUMENTS

| | | | |
|---|---|---|---|
| 5,152,991 A | 10/1992 | Vogel et al. | |
| 6,309,629 B1 | 10/2001 | Travkina et al. | |
| 6,423,306 B2 * | 7/2002 | Caes et al. | 424/78.02 |
| 2005/0197479 A1 * | 9/2005 | Pavlin | 528/64 |
| 2007/0031361 A1 | 2/2007 | Herrmann et al. | |

FOREIGN PATENT DOCUMENTS

| | | |
|---|---|---|
| FR | 2 785 530 A1 | 5/2000 |
| JP | 64-061409 A | 3/1989 |
| JP | 1992243842 A | 8/1992 |
| JP | 2001-518929 A | 10/2001 |
| JP | 2002-284645 A | 10/2002 |
| JP | 2003-137733 A | 5/2003 |
| JP | 2003516949 A | 5/2003 |
| JP | 2006342163 A | 12/2006 |
| WO | 98/42298 A1 | 10/1998 |

OTHER PUBLICATIONS

Vapor Pressure of Mineral Oil accessed via ttp://www.finalube.com/reference_material/Vapor_Pressure_Of_Mineral_Oil.htm on Jun. 26, 2012.*
Edwards Oils created: Mar. 8, 2007 accessed via http://www.edwards.co.il/catalog/13/130302.pdf on Jun. 26, 2012.*
International Search Report dated May 9, 2008.
Database WPI Week 200382, Derwent Publications Ltd., London, Great Britain, XP-002451756.
Database WPI Week 200403, Derwent Publications Ltd., London, Great Britain, XP-002451757.
Japanese Office Action, dated Feb. 5, 2013, from corresponding Japanese application.

* cited by examiner

*Primary Examiner* — Kortney L Klinkel
(74) *Attorney, Agent, or Firm* — Young & Thompson

(57) ABSTRACT

A cosmetic composition in the form of a water-in-oil emulsion includes a fatty phase and an aqueous phase, the fatty phase of which includes at least one hydrocarbon oil, at least one first copolymer of ethylene and of propylene and at least one second copolymer of styrene and of at least one olefin other than styrene. A cosmetic method for caring for or making up skin or the lips, and the topical application to the lips of this composition are also disclosed.

19 Claims, No Drawings

COMPOSITION FOR MAKING UP THE LIPS

The present invention relates to a cosmetic composition in the form of a water-in-oil emulsion comprising at least one non volatile hydrocarbon oil, at least one first copolymer of ethylene and of propylene, and at least one second copolymer of styrene and of at least one olefin other than styrene.

It also relates to a cosmetic method for caring or making up the face comprising the topical application of this composition on the keratinous material.

The present invention deals with compositions for making up the skin, nails, eyelashes, eyebrows, or the lips, such as foundations, eyeshadows, lipsticks, lip gloss products, products for concealing rings under the eyes, blushers, mascaras, eyeliners, lip pencils, eyeliner pencils, nail varnishes.

According preferred embodiments, the cosmetic composition is a lip gloss product, a foundation base or a product for the styling of eyebrows.

One aim of the present invention is to provide a cosmetic composition giving a fresh feeling upon application, having a good wear during the day, and having a good level of transparency.

The product is preferably non opaque, it means it is transparent or translucent.

A way to obtain cosmetic products having a good wear on keratinous materials is usually to include significant proportions of volatile oils. Nevertheless, such large amount of volatile oils decrease comfort and gloss of said compositions.

One aim of the present invention is to provide a cosmetic composition giving a fresh feeling upon application, having a good wear during the day, and having a minimum gloss effect. According one embodiment, the composition according to the invention contains low amounts of volatile oils and still performs good wear on lips or skin.

In this context, the aim of the present invention is to provide a composition for making up the skin, the eyebrows or the lips, which is translucent or transparent, and provides a freshening feeling to the consumer when applied on the keratinous material.

In order to solve this problem, the Applicant has looked for a water-in-oil emulsion containing non volatile hydrocarbon. He has surprisingly found that the mixture of two specific copolymers makes it possible to lower the refractive index of a fatty phase comprising a non volatile hydrocarbon oil to bring it closer to that of an aqueous phase.

The aim of the present invention is achieved by the use, in an emulsion of water-in-oil type comprising a non volatile hydrocarbon oil, of a combination of at least two specific copolymers.

A subject-matter of the present invention is thus a cosmetic composition in the form of a water-in-oil emulsion comprising at least one non volatile hydrocarbon oil, at least one first copolymer of ethylene and of propylene and at least one second copolymer of styrene and of at least one olefin other than styrene.

The water-in-oil emulsion includes a fatty phase and an aqueous phase, and the fatty phase preferably comprises at least one non volatile hydrocarbon oil, at least one first copolymer of ethylene and of propylene, and at least one second copolymer of styrene and of at least one olefin other than styrene.

For greater transparency, the refractive index of the aqueous phase can advantageously be increased by providing for the aqueous phase to include at least one polyol. Polyglycerol-6 is preferred in so far as it brings about a big increase in the refractive index of the aqueous phase.

Non Volatile Hydrocarbon Oil

As indicated above, the composition includes at least one non volatile hydrocarbon oil.

Within the meaning of the present invention, the term "oil" is understood to mean a compound which is liquid at ambient temperature (25° C.) and which, when it is introduced in a proportion of at least 1% by weight into water at 25° C., is not at all soluble in water or soluble to a level of less than 10% by weight, with respect to the weight of oil introduced into the water.

The term "hydrocarbon oil" is understood to mean an oil comprising hydrogen and carbon atoms, and containing no silicon atoms.

Within the meaning of the present invention, the term "non volatile oil" is understood to mean an oil which has a vapour pressure at ambient temperature and atmospheric pressure, lower that 0.13 Pa ($10^{-3}$ mm Hg).

Hydrocarbon oils having a low or moderate polarity are preferred, such as ester oils bearing no polar groups and hydrocarbure oils.

When intended for lip application, the hydrocarbon oil preferably have a high refractive index, typically above 1.45, or even above 1.47.

The non volatile hydrocarbon oil present in the composition according to the invention may be chosen from hydrocarbures, i.e. oils made of carbon and hydrogen atoms. It can in particular be chosen from polybutene, hydrogenated polyisobutene and hydrogenated polydecene. It is preferably hydrogenated polydecene.

According to the invention, the non volatile hydrocarbon oils can also be chosen chosen from esters of monocarboxylic acids preferably monoesters.

Advantageously, said esters correspond to the following formula (I):

$$R_1\text{—CO—O—}R_2 \qquad (I)$$

where $R_1$ represents a linear or branched alkyl radical of 1 to 40 carbon atoms, preferably of 7 to 19 carbon atoms, optionally comprising one or more ethylenic double bonds, and optionally substituted, $R_2$ represents a linear or branched alkyl radical of 1 to 40 carbon atoms, preferably of 3 to 30 carbon atoms and even better of 3 to 20 carbon atoms, optionally comprising one or more ethylenic double bonds.

$R_2$ can also represent an aryl radical, for example benzyl.

The number of carbon of said ester preferably goes from 10 to 40, and is typically around 20.

$R_1$ may represent the residue of a preferably higher, linear or, preferably branched fatty acid comprising from 1 to 40 and even better from 7 to 19 carbon atoms and $R_2$ may represent a linear or preferably branched hydrocarbon chain containing from 1 to 40, preferably from 3 to 30 and even better from 3 to 20 carbon atoms. Examples of $R_1$ groups are those derived from fatty acids chosen from the group consisting of acetic, propionic, butyric, caproic, caprylic, pelargonic, capric, undecanoic, lauric, myristic, palmitic, stearic, isostearic, arachidic, behenic, oleic, linolenic, linoleic, oleostearic, arachidonic and erucic acids, and mixtures thereof.

Examples of esters which can be used in the fatty phases of the compositions of the invention are for example purcellin oil (cetostearyl octanoate), isononyl isononanoate, isopropyl myristate, isopropyl palmitate, 2-ethylhexyl palmitate, C12-C15 ester benzoate, 2-octyldodecyl stearate, 2-octyldodecyl erucate, isostearyl isostearate, and heptanoates, octanoates, decanoates or ricinoleates of alcohols or polyalcohols, for example of fatty alcohols.

The ester oil will be preferably chosen from the following compounds:
- isononyl isononanoate,
- isopropyl palmitate,
- isostearyl isostearate.

The non volatile hydrocarbon oil amount advantageously goes from 5 to 35% by weight of the total weight of the composition, preferably from 10 to 30% by weight of the total weight of the composition.

First Copolymer

The first copolymer can be an ethylene/propylene copolymer in dispersion in a non volatile hydrocarbon oil. Said non volatile hydrocarbon oil can be one of the oils described hereabove.

As an example, first copolymer can be an ethylene/propylene copolymer in dispersion in hydrogenated polydecene, such as those sold in particular by Créations Couleurs under the trade name Creagel® crystal, and in particular Creagel® crystal AF.

The amount of first copolymer goes advantageously from 0.1 to 10% by weight of the total weight of the composition, preferably from 0.5 to 5%.

Second Copolymer

The second copolymer can more particularly be a diblock or triblock copolymer or a copolymer comprising radial blocks. These copolymers generally do not comprise a monomer other than olefins, so that they are preferably chosen from olefin copolymers comprising a styrene monomer.

The second copolymer can in particular comprise, as olefin other than styrene, at least one olefin chosen from ethylene, propylene, butylene, butadiene and isoprene, without this list being limiting.

The second copolymer can in particular be chosen from
- ethylene/propylene/styrene,
- butylene/ethylene/styrene,
- butadiene/styrene,
- isoprene/styrene,
- styrene/butadiene/styrene,
- styrene/isoprene/styrene,
- styrene/ethylene/butylene/styrene copolymers,
- and their blends.

The second copolymer can in particular be chosen from copolymers sold by Shell under the trade name Kraton®: Kraton G1701 X, G1652, D1102, D1107, D116, or by Penreco under the trade name Versagel®: Versagel® MN, ME, MP, ML.

The second copolymer can be dispersed in a non volatile hydrocarbon oil, before mixing with the other ingredients of the composition. Said non volatile hydrocarbon oil can be one of the oils described hereabove.

As an example, second copolymer can be a blend of ethylene/propylene/styrene copolymer and butylene/ethylene/styrene copolymer.

The first and second copolymers are preferably included in the fatty phase of the water-in-oil emulsion according to the invention.

The ratio of second to first copolymer goes advantageously from 1/10 to 20/1, more preferably from 1/2 to 5/1, preferably from 1/1 to 2/1.

The amount of second copolymer goes advantageously from 0.1 to 10% by weight of the total weight of the composition, preferably from 0.5 to 5%.

Other Ingredients

Apart from the non volatile hydrocarbon oil, the water-in-oil emulsion according to the invention can include at least one other oil chosen in particular from: synthetic (poly)esters and (poly)ethers, vegetable oils, branched and/or unsaturated fatty acids, such as octyldodecanol, branched and/or unsaturated fatty alcohols, silicone oils, such as linear polydimethylsiloxanes, which are optionally phenylated, or cyclic polydimethylsiloxanes, fluorosilicone oils, fluorinated oils, and their mixtures.

The amount of oils present in the composition including said non volatile hydrocarbon oil preferably represents more than 20%, more preferably more than 25%, of the total weight of this composition, for example between 20 and 50%, preferably between 25 and 40%, more preferably between around 30% and around 35%.

Among the oils of the composition, it is preferable to use, in the present invention, at least one glossy oil, that is to say an oil exhibiting a refractive index of greater than 1.45 and preferably of greater than 1.47.

Examples of glossy oils are in particular phenylated silicone oils, such as those identified by the INCI name "phenyl trimethicone", an example of which is composed of the silicone available under the trade name Mirasil P™ from Rhodia, those identified by the INCI name "phenylpropyldimethylsiloxysilicate", an example of which is composed of the silicone available under the trade name Silshine 151 from General Electric, and those identified by the INCI name "trimethyl pentaphenyl trisiloxane", an example of which is composed of the silicone available under the trade name DC PH 1555 HRI from Dow Corning.

Mention may also be made, as glossy oils, of the fluorinated silicones identified by the INCI name "perfluorononyl dimethicone", an example of which is composed of the silicone available under the trade name Pecosil FS (FSU, FSL, and the like) from Phoenix and another example of which is composed of the silicone available under the trade name Biosil Basics (Fluorosil LF, 14, and the like) from Biosil Technologies.

Other examples of glossy oils are natural oils and in particular castor seed oil; mono- and polyesters of fatty acids and/or of fatty alcohols, the fatty chain of which includes from 6 to 20 carbon atoms, in particular: mono- and polyesters of hydroxy acids and of fatty alcohols, such as diisostearyl malate, esters of benzoic acid and of fatty alcohols, such as $C_{12}$-$C_{15}$ alkyl benzoate, polyesters of polyols and in particular of (di)pentaerythritol, such as pentaerythrityl tetraisostearate, dipentaerythrityl pentaisononanoate and dipentaerythrityl $C_5$-$C_9$ esters, or of polyglycerol, such as that known under the INCI name "bis-diglyceryl polyacyladipate-1" and sold by Sasol under the trade name Softisan 645, or of trimethylolpropane, such as trimethylolpropane triethylhexanoate, which is sold in particular by Kokyu Alcohol Kogyo under the trade name Kak TTO, or of propylene glycol, such as propylene glycol dibenzoate, which is sold in particular by Inolex under the trade name Lexfeel Shine, and isocetyl stearoyl stearate; and polyesters of hydrogenated castor oil, such as the esters sold by Kokyu Alcohol Kogyo under the trade names Risocast DA-H and Risocast DA-L.

It is clearly understood that the composition according to the invention can comprise mixtures of the oils mentioned above.

The composition employed according to the invention can additionally include at least one volatile oil. The amount of volatile oil is preferably low, typically lower than 15% by weight of the total weight of the composition, more preferably lower than 10% by weight of the total weight of the composition, even more preferably between 5 and 8% by weight of the total weight of the composition. The composition may be free of volatile oil.

The term "volatile oil" is understood to mean an oil which has a nonzero vapour pressure at ambient temperature and atmospheric pressure, in particular which has a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

The volatile oil can be a silicone oil, a hydrocarbon oil, a fluorinated oil or a mixture of such oils.

The term "silicone oil" is understood to mean an oil comprising at least one silicon atom and in particular at least one Si—O group.

Examples of volatile silicone oils or volatile silicones are in particular the linear or cyclic silicone oils having a viscosity of less than 8 centistokes ($8\times10^{-6}$ mVs) and including in particular from 2 to 10 silicon atoms, more particularly from 2 to 7 silicon atoms, these silicones optionally comprising alkyl or alkoxy groups comprising from 1 to 10 carbon atoms. Mention may in particular be made, as volatile silicone oil which can be used in the invention, of some dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, the compounds identified by the INCI names methyl trimethicone and caprylyl methicone, and their mixtures. Cyclic silicone oils are preferred in the present invention.

Volatile hydrocarbon oils can be chosen from hydrocarbon oils comprising from 8 to 16 carbon atoms, in particular branched $C_8$-$C_{16}$ alkanes (also known as isoparaffins), such as isododecane (also known as 2,2,4,4,6-pentamethylheptane), isodecane or isohexadecane.

The term "fluorinated oil" is understood to mean an oil comprising at least one fluorine atom, such as nonafluoromethoxybutane, perfluoromethylcyclopentane, perfluorodimethylcyclohexane, perfluoroperhydrophenanthrene, perfluorodecalin, and their mixtures, without this list being limiting.

The fatty phase of the water-in-oil emulsion according to the invention can in addition advantageously include at least one fatty-phase structuring agent, such as a wax, a paste, a lipophilic gelling agent or their mixtures.

The term "wax" is understood to mean a fatty substance which has a melting point of greater than 30° C. and generally of less than 90° C., which is liquid under the conditions of preparation of the composition and which exhibits, in the solid state, an anisotropic crystalline arrangement. Examples of waxes are in particular vegetable, mineral or synthetic waxes, it being possible for the latter advantageously to be hydrocarbon or silicone waxes. Mention may thus be made of carnauba wax, candelilla wax, beeswax (Cera alba), polyethylene wax and paraffin wax, as well as ozokerites and triesters of $C_8$-$C_{20}$ acids and of glycerol, such as glyceryl tribehenate, and their mixtures, without this list being limiting.

Examples of lipophilic gelling agents are in particular silicone polymers and more particularly organopolysiloxane elastomers. Mention may be made, among these, of the at least partially crosslinked polymers resulting from the reaction of an organopolysiloxane carrying unsaturated groups, such as vinyl or allyl groups, situated at the end of or in the middle of the chain, preferably on a silicon atom, with another reactive silicone compound, such as an organohydropolysiloxane. These polymers are usually available in gel form in a volatile or non-volatile silicone solvent or in a hydrocarbon solvent. Examples of such elastomers are sold in particular by Shin-Etsu under the trade names KSG-6, KSG-16, KSG-31, KSG-32, KSG-41, KSG-42, KSG-43 and KSG-44 and by Dow Corning under the trade names DC 9040 and DC 9041. Another oily gelling agent is composed of a silicone polymer, obtained by self polymerization in the presence of a catalyst of an organopolysiloxane functionalized by epoxy groups and hydrosilylated, which is available commercially from General Electric under the trade name Velvesil 125. Another lipophilic gelling agent is composed of a cyclic vinyldimethicone/dimethicone copolymer, such as that sold by Jeen under the trade name Jeesilc PS (including PS-VH, PS-VHLV, PS-CM, PS-CMLV and PS-DM).

Another type of lipophilic gelling agent is composed of polyamides, such as those identified by the INCI name polyamide-3 and in particular the Sylvaclear AF 1900V and PA 1200V polymers available from Arizona Chemicals, and also those identified by the INCI name "Ethylenediamine/Hydrogenated Dimer Dilinoleate Copolymer Bis-Di-C14-18 Alkyl Amide" and available, for example, under the trade name Sylvaclear A200V or Sylvaclear A2614V from Arizona Chemical. In an alternative form, the lipophilic gelling agent can be a bentone or a sucrose ester, such as that denoted by the INCI name "Sucrose tetrastearate triacetate".

The fatty phase can also include one or more pasty compounds, that is to say lipophilic fatty substances which, like the waxes, are capable of undergoing a reversible liquid/solid change in state and have, in the solid state, an anisotropic crystalline arrangement but which differ from the waxes in that they include, at a temperature of 23° C., a liquid fraction and a solid fraction.

In addition, it can comprise at least one film-forming polymer capable of introducing hold and/or transfer-free properties and/or gloss to the makeup conferred by the composition. It can in particular be a silicone polymer optionally modified by urethane or fluorine or acrylate, such as the (meth)acrylate silicones sold by Shin-Etsu under the trade names KP-545, KP-561 and KP-562, or the polymers sold by Dow Corning under the trade names DC FA 4002 ID and DC FA 4001 CM. Other examples of film-forming polymers are silicone resins and in particular MQ resins, such as trimethylsiloxysilicates, and MT resins, such as silsesquioxane derivatives and in particular polymethylsilsesquioxanes, sold in particular by Shin-Etsu, and also the polypropylsilsesquioxanes sold by Dow Corning under the trade name DC 670 or the phenylpropylpolysilsesquioxane sold by Wacker under the trade name Belsil SPR45VP. Another example is composed of fluorosilicone polymers identified by the INCI name "Trifluoropropyldimethylsiloxy Triethylsiloxysilicate", such as that sold by General Electric under the trade name XS66-B8226. Use may also be made, as film-forming polymers, of bioadhesive polymers obtained, for example, by polycondensation of dimethiconol and of MQ silicate resin in a solvent, such as heptane, which are sold in particular by Dow Corning under the trade names DC7-4405 low tack and DC7-4505 high tack. Other examples of film-forming polymers are poly(cyclic olefins), such as polycyclopentadiene, sold in particular by Kobo under the trade name Koboguard 5400, or also polydicyclopentadiene. Yet other examples of film-forming polymers are composed of copolymers of vinylpyrrolidone (VP) and/or of linear olefins, such as VP/hexadecene and VP/eicosene copolymers, including Antaron V216 and Antaron V220 from ISP, or also ethylene/vinyl acetate copolymers, such as AC 400 from Baerlocher. Other film-forming polymers capable of being used in this invention are polyacrylates, such as poly(ethyl acrylate), sold in particular by Creations Couleurs under the trade name Creasil 7 ID.

The water-in-oil emulsion according to the invention includes, in addition to the fatty phase described above, an aqueous phase comprising water and optionally hydrophilic and/or water-soluble additives, such as polyol.

The aqueous phase of the water-in-oil emulsion preferably represents from 30 to 60% by weight of the total weight of the composition, preferably from 40 to 50% by weight of the total weight of the composition.

According to a preferred embodiment, the composition according to the invention includes from 5 to 30% by weight, preferably from 10 to 20% by weight, of water, with respect to the total weight of the composition.

For greater transparency, the refractive index of the aqueous phase can advantageously be increased by including at least one polyol in the aqueous phase. Polyol is understood to mean a polymeric or nonpolymeric compound including at least two hydroxyl groups.

Polyol can advantageously be a polyglycerol derivative such as an industrially produced, commercially available product, such as polyglycerol #310 (manufactured by Sakamoto Yakuhin Kogyo Co., Ltd.), polyglycerol #500 (manufactured by Sakamoto Yakuhin Kogyo Co., Ltd.), polyglycerol #750 (manufactured by Sakamoto Yakuhin Kogyo Co., Ltd.), diglycerol (manufactured by Sakamoto Yakuhin Kogyo Co., Ltd.)

Polyol which can be used comprise glycols, such as propylene glycol, dipropylene glycol and butylene glycol; glycerol; monosaccharides, such as glucose and fructose; sorbitol; disaccharides, such as sucrose (or saccharose); homopolymers of glycols, such as poly(ethylene glycol)s and poly(propylene glycol)s; homopolymers of glycerol or polyglycerols; and their mixtures.

Sucrose, polyglycerol and their mixtures are preferred for use in the present invention.

In particular, the polyglycerol can comprise from two to ten glycerol units on average. Polyglycerol-6 is preferred The polyglycerol content is advantageously comprised between 1 and 10% by weight, typically around 5% by weight of the weight of the composition.

The polyol or mixture of polyol can represent from 5 to 40% by weight, preferably 10 to 35%, for example from 25 to 30% by weight of the total weight of the composition.

In addition to water and the possible polyols described above, the aqueous phase of the water-in-oil emulsion according to the invention can comprise hydrophilic or lipophilic active principles, hydrophilic latexes or at least one hydrophilic gelling agent. The hydrophilic gelling agent is preferably a hydrocolloid which can in particular be chosen from: homo- and copolymers of acrylic acid and/or of salts or of esters of acrylic acid, such as carbomers, homo- and copolymers of acrylamide, homo- and copolymers of acryloylamidomethylpropanesulphonic acid (AMPS), such as Aristoflex® AVC or HMB from Clariant, guar or xanthan gums and cellulose derivatives, without this list being limiting.

The composition according to the invention can also comprise one or more water-in-oil emulsifiers preferably chosen from non-ionic surfactants, such as polyethoxylated dipolyhydroxystearate (30 EO), sold in particular under the trade name Arlacel® P135 by Uniqema; or also polysiloxanes modified by polyethers, without this list being limiting.

The composition used according to the invention can additionally include at least one filler. This term is understood to mean any inorganic or organic particle of any shape (in particular spherical or lamellar) which is insoluble in the composition. Examples of fillers are talc, mica, silica, kaolin, boron nitrite, starch, starch modified by octenylsuccinic anhydride, polyamides, silicone resins, powders derived from silicone elastomers and powders derived from acrylic polymers, in particular from poly(methyl methacrylate). The fillers can in particular be composed of several layers of different chemical nature and/or of different physical form and can in particular be provided in the form of lamellae coated with spherical fillers. They can be modified using various surface treatments. An example of a surface-treated filler is composed of silica modified by an ethylene/methacrylate copolymer, sold in particular by Kobo under the trade names DSPCS 20N-I2, DSPCS/3H-I2 and DSPCS-I2.

The composition can also comprise at least one colouring material chosen from water-soluble or fat-soluble dyes, fillers having the effect of colouring and/or opacifying the composition and/or of colouring the lips, such as pigments, pearlescent agents, lakes (water-soluble dyes adsorbed on an inert inorganic carrier), and their mixtures. These colouring materials can optionally be treated at the surface with a hydrophobic agent, such as silanes, silicones, fatty acid soaps, $C_{9-15}$ fluoroalkyl phosphates, acrylate/dimethicone copolymers, mixed $C_{9-15}$ fluoroalkyl phosphate/silicone copolymers, lecithins, carnauba wax, polyethylene, chitosan and optionally acylated amino acids, such as lauroyl lysine, disodium stearoyl glutamate and aluminium acyl glutamate. The pigments can be inorganic or organic and natural or synthetic. Examples of pigments are in particular iron, titanium or zinc oxides, and also composite pigments and goniochromatic, pearlescent, interferential, photochromic or thermochromic pigments, without this list being limiting. The pearlescent agents can be chosen from those conventionally present in makeup products, such as mica-titanium dioxide products.

The composition can comprise pigments, pearls and/or fillers. As inorganic pigments which can be used in the invention, mention may be made of titanium, zirconium or cerium oxide, as well as zinc, iron or chromium oxide and ferric blue.

Among the organic pigments which can be used in the invention, mention may be made of carbon black and barium, strontium, calcium (DC Red No. 7) and aluminium lakes.

Among the pearlescent agents which can be used in the invention, mention may be made of mica coated with titanium oxide, with iron oxide, with natural pigment or with bismuth oxychloride, such as coloured titanium mica.

The fillers can be present in a proportion of from 0 to 35% of the total weight of the composition, preferably 0.5 to 15%. Mention may be made in particular of talc, mica, kaolin, Nylon powders (Orgasol® in particular) and polyethylene powder, Teflon, starch, boron nitride, copolymer microspheres such as Expancel® (Nobel Industrie), Polytrap® (Dow Corning) and silicone resin microbeads (Tospearl® from Toshiba, for example).

The amount of colouring agent is preferably rather low, typically below 10% by weight of the total weight of the composition, for example between 1 and 5% by weight, so that transparency of the composition be not impaired.

The composition according to the invention can also include sodium saccharinate; antioxidants, such as alkyl or phosphoryl esters of ascorbic acid, or also tocopherol and its esters; sequestering agents, such as EDTA salts; pH adjusters; preservatives; and fragrances.

The composition according to the invention can also include one or more active ingredients chosen from the following lists, such as agents stimulating vasodilatation or freshening agents.

An example of plumping agents is HYALURONIC FILLING SPHERES.

Hydrating agents can be chosen from: Ceretonia Siliqua fruit extract, Crithmum Maritum extract, Lavender wax, marine juice, Camellia flower water, Lotus water, Orange flower wax (*citrus aurantium*), Jasmine wax (*jasminum gran-*

*diflorum*), DECOX® (4-decyloxazolidin-2-one), HYDRATYL® LS 8453 and Lipofructyl Argan®.

Examples of procollagen agents are as follows: Opal Powder®, Peptides such as M300®, Maxi Lip®, DERMICAN®, *Pisum sativum* extract, *Zingiber purpureum* rhizome extract, *Guazuma ulmifolia* extract, *Canarium commune* Gum-resin, hydrolyzed soybean protein, hydroxyproline, METHYLSILANOL MANNURONATE, HYDROXYPROSILISILANE, hydrolyzed *Cucurbita Pepo* seedcake, *Centella asiatica* extract, Keep young commiphora jasmine Aquaphylline (*viola tricolour* extract).

Essential oils can be chosen cinnamon, ginger oil, black pepper oil, chili pepper leaves oil, pepper mint oil, clove oil, or one of their mixtures.

In particular, agents stimulating vasodilatation, and/or having anticoagulant activity and/or antihypertensive effect can be:
  Antihypertensives agents, such as Potassium-channel openers;
  Phosphodiesterases inhibitors, such as visnadine, esculoside, icarine or extracts containing them, as described in WO 2005/004858;
  Flavonoïds or flavoglycosides;
  Glucosides;
  Plant extracts or peptides having vasodilatory properties.

Antihypertensive agents can be thiazides; angiotensin receptor inhibitors, such as losartan or candesartan; prostaglandins for example E prostaglandins and prostacyclines; ACE inhibitors, such as captopril or ramipril; Potassium-channel openers such as minoxidil, cromakalim, diazoxide, nicorandil, pinacidil or derivatives thereof; Calcium Channel Blockers such as nifedipine, verapamil, diltiazem, amlodipine; adrenergic receptors blockers such as niacine, prazosine, hydralazine; acetylcholine, and muscaric receptors activators.

Flavonoids and flavoglycosids can be for example *Ginkgo* flavoglycosids, amentoflavone, *Gingko biloba* flavones in free form or *Gingko biloba* flavones complexed with phospholipids as described in WO 2005/0048584; hesperidine, alpha-G-hesperidine, hesperidine methyl chalcone, rutosides (ex: betahydroxyéthyl-rutoside, triméthyl-rutoside).
Vasodilatory Plant Extracts:
  *Helichrysum italicum* extract as described in WO 03/018730; *Ribes nigrum* extracts, *Epimedium grandiflora* extract), *Actinidia chinensis L.* extract, *Cupressus sempervirens* extract, *Melissa officinalis* extract, *Vinca minora* extract, *Centella asiatica* extract, *Terminalia sericea, Calendulae* extracts, *Arnica* extracts, *Ammi visnaga* extracts.
Vasodilatory Peptides:
  CGRP (Calcitonin gene related peptide), substance P (decapeptide liberated by nerve termination) or VIP (Vasoactive Intestinal Polypeptide) as described in EP 225 639.
Other Vasodilatory Agents:
  Niacine and derivatives thereof such as esters of nicotinic acid (xanthinol nicotinate, inositol nicotinate); salicylic acid and esters thereof; dihydroergotoxine méthanesulfonate; dihydroergocomine méthanesulfonate, dihydroergocristine méthanesulfonate, cinnarizine, vincamine, pentoxifylline, baméthane sulfate, bencyclane hydrogénofumarate, béta-pyridylcarbinol; Precursors of the Nitric Oxide Donor (NO), non polymeric NO liberators; les stimulateurs de la synthèse et/ou de l'activité des NO Synthases (NOS) Stimulators and mixtures thereof.

Agents for temperature modulation can be a freshening agent, as for example menthol, mint extracts or mint essential oils; peppermint oil, wintergreen oil, menthone, menthyl lactate, menthane derivatives, such as menthane carboxamides N-ethyl P-menthane Carboxamide-3, 3-(1-methoxy)-propane-1,2-diol, p-menthane-3,8-diol, menthyl succinate; aloe vera essential oils or ginseng essential oils.

Freshening agent can comprise an endothermic organic salt such as potassium chloride, or urea.

Agents for temperature modulation can be warming agent such as camphor, eucalyptus extract or essential oils, ginseng essential oils.

Microcirculation activating agents can be chosen from Biomoduline (*Lentinus edodes*), Ruscogenine, Yuzu water (*citrus junos*), VISNADEX® (visnadine), Kombuchka, Pycnogénol, manganese gluconate (Givobio GMn® from Seppic), Visnadine (from Indena), lupin extracts (Eclaline from Silab), Epaline® 100 (Laboratoires Carilène), Bigarade flowers extract (Remoduline® from Silab), vitamine P as derivatives thereof such as Permethol® (from Sochibios), *ruscus* extracts, ginseng extracts, ivy extracts, sweet clover extracts, caffeine, nicotinate and derivatives thereof, lysine and derivatives thereof (Asparlyne® from Solabia).

Compositions according to the invention can in addition comprise at least one UV screening agent chosen from organic and inorganic screening agents and their mixtures. Mention may in particular be made, as organic screening agents, of dibenzoylmethane derivatives (including butyl methoxydibenzoylmethane), cinnamic acid derivatives (including ethylhexyl methoxycinnamic), salicylates, para-aminobenzoic acids, $\beta,\beta$-diphenylacrylates, benzophenones, benzylidenecamphor derivatives, phenylbenzimidazoles, triazines, phenylbenzotriazoles and anthranilic derivatives. Mention may in particular be made, as inorganic screening agents, of screening agents based on inorganic oxides in the form of pigments or nanopigments which may or may not be coated and in particular based on titanium dioxide or on zinc oxide.

Examples of additional adjuvants are mentioned in particular in the CTFA dictionary (International Cosmetic Ingredient Dictionary and Handbook published by The Cosmetic, Toiletry and Fragrance Association, $9^{th}$ Edition, 2002).

The composition according to the invention can be provided in particular in the form of a thick fluid packaged in a container provided with an applicator, generally made of foam, in the form of a fine brush or coarse brush. Of course, other methods of application are possible, in particular employing applicators of felt type.

Preferably, the composition employed according to the invention is used as product for making up the lips, in particular as lip gloss.

Another subject-matter of the present invention is thus a cosmetic method for caring for or making up the lips, comprising the topical application, to the lips, of the composition as described above.

The invention will now be illustrated by the following non limiting examples.

EXAMPLES

Example 1

Lip Gloss

A lip gloss was manufactured in a way conventional to a person skilled in the art, which lip gloss has the following composition in which the proportions of the ingredients are expressed as percentages by weight:

| INCI name/type | Massic % |
|---|---|
| Hydrogenated polydecene | 25.1% |
| ethylene/propylene/styrene copolymer | 2.0% |
| butylene/ethylene/styrene copolymer | 0.3% |
| ethylene/propylene copolymer | 2.6% |
| Cyclomethicone (D6) | 3% |
| PEG-30 dipolyhydroxystearate Arlacel P135 (Uniqema) | 3% |
| Octyldodecanol & disteardimonium hectorite & propylene carbonate Bentone Gel EUG V (Elementis) | 3% |
| Octyldodecanol Eutanol G (Cognis) | 2.4% |
| Butylene glycol & menthyl PCA & octyl dodecyl PCA Cryogenyl (Solabia) | 1.2% |
| Polyglyceryl-6 | 5% |
| Sodium chloride | 0.5% |
| Sucrose tetrastearate triacetate Sisterna A10E-C (Unipex) | 2% |
| Preservatives | 1.1% |
| Antioxidants | 0.7% |
| UV screening agents | 8% |
| Dyes | 1.1% |
| Sucrose | 25% |
| Water | Qsp 100% |

In a preferred embodiment, ethylene/propylene/styrene copolymer, butylene/ethylene/styrene copolymer, and ethylene/propylene copolymer are pre-mixed separately or together in hydrogenated polydecene, to form a gel that is further included with the rest of the ingredients.

For example, a gel of ethylene/propylene copolymer in hydrogenated polydecene can be used: such a gel is sold under the reference Creagel Crystal AF by Créations Couleurs.

Sensory Evaluation

The formulation of Example 1, packaged in a small bottle, was evaluated by a panel of 20 subjects under standardized conditions of temperature, hygrometry and light.

In order to do this, the product was applied to the lower lip using the fine applicator brush with which the small bottle is equipped, the outline of the lip being drawn well. The fine brush was subsequently immersed in the composition before applying the product to the upper lip in the same way.

The members of the panel evaluated the product on application and after application according to descriptors with which they were provided.

The data were subsequently collected and analysed using Fizz software according to the statistical methods specific to profile tests. The results obtained are collated in the following table:

| Attribute | Mean value (/10) | Standard deviation |
|---|---|---|
| Slip on application | 7.0 | 0.6 |
| Softness on application | 7.9 | 0.8 |
| Softness of the lips after application | 7.3 | 0.8 |
| Gloss | 6.4 | 1.4 |
| Tackiness | 1.9 | 1.1 |
| Opacity on the lips | 1.9 | 1.6 |
| Thickness of the film | 3.4 | 1.6 |

It is thus found that the composition according to the invention is applied to the lips with very good slip and forms, on the lips, a thin, soft, glossy and nontacky film which leaves the lips visible (translucent).

Example 2

Foundation Base

| Phase | INCI name | % massic |
|---|---|---|
| A | OCTYLDODECANOL | 7.1 |
|   | CYCLOMETHICONE (DOW CORNING 246) | 8 |
|   | HYDROGENATED POLYDECENE | 12.6 |
|   | ETHYLENE/PROPYLENE/STYRENE COPOLYMER | 1.3 |
|   | BUTYLENE/ETHYLENE/STYRENE COPOLYMER | 0.2 |
|   | ETHYLENE/PROPYLENE COPOLYMER | 0.9 |
|   | PEG-30 DIPOLYHYDROXYSTEARATE (ARLACEL P135) | 3 |
|   | OCTYLDODECANOL & DISTEARDIMONIUM HECTORITE & PROPYLENE CARBONATE (BENTONE GEL EUG V) | 3 |
|   | PEG-8 & TOCOPHEROL & ASCORBYL PALMITATE & ASCORBIC ACID & CITRIC ACID (OXYNEX K) | 0.2 |
|   | preservatives | 1.1 |
|   | TOCOPHERYL ACETATE | 0.5 |
|   | ETHYLHEXYL METHOXYCINNAMATE (PARSOL MCX) | 5 |
| B | OCTYLDODECANOL | 5 |
|   | IRON OXIDES | 1.55 |
|   | TITANIUM DIOXIDE | 1.65 |
| C | SUCROSE TETRASTEARATE TRIACETATE (SISTERNA A10E-C) | 3 |
| D | WATER | Qsp 100 |
|   | POLYGLYCERIN-6 (polyglycerol #500 from Sakamoto) | 5 |
|   | SUCROSE | 20 |
|   | SODIUM CHLORIDE | 0.5 |
|   | MICA & IRON OXIDES & TITANIUM DIOXIDE (TIMICA GOLDEN BRONZE) | 0.3 |

In a preferred embodiment, ethylene/propylene/styrene copolymer, butylene/ethylene/styrene copolymer, and/or ethylene/propylene copolymer are pre-mixed separately or together in hydrogenated polydecene, to form a gel that is further mixed with the rest of the ingredients.

For example, a gel of ethylene/propylene copolymer in hydrogenated polydecene can be used: such a gel is sold under the reference Creagel Crystal AF by Créations Couleurs.

The invention claimed is:
1. A transparent or translucent cosmetic composition in the form of a water-in-oil emulsion comprising at least one non volatile hydrocarbon oil, at least one first copolymer consisting of ethylene and of propylene, at least one second copolymer of styrene and of at least one olefin other than styrene and a polyol selected from homopolymers of glycerol, wherein the at least one non volatile hydrocarbon oil is selected from non-volatile oils consisting of carbon and of hydrogen or non-volatile esters of monocarboxylic acids.

2. The composition according to claim 1, wherein the at least one olefin of the at least one second copolymer made of styrene and of at least one olefin is selected from the group consisting of ethylene, propylene, butylene, butadiene, isoprene and mixtures thereof.

3. The composition according to claim 1, wherein the second copolymer is selected from the group consisting of:
ethylene/propylene/styrene,
butylene/ethylene/styrene,
butadiene/styrene,
isoprene/styrene,
styrene/butadiene/styrene,
styrene/isoprene/styrene,
styrene/ethylene/butylene/styrene copolymers,
and blends thereof.

4. The composition according to claim 1, wherein the second copolymer is a blend of ethylene/propylene/styrene and butylene/ethylene/styrene copolymers.

5. The composition according to claim 1, wherein the ratio of second to first copolymer is from 1/10 to 20/1.

6. The composition according to claim 1, wherein the amount of first copolymer is from 0.1 to 10% by weight of the total weight of the composition.

7. The composition according to claim 1, wherein the amount of second copolymer is from 0.1 to 10% by weight of the total weight of the composition.

8. The composition according to claim 1, wherein the non volatile hydrocarbon oil amount is from 5 to 35% by weight of the total weight of the composition.

9. The composition according to claim 1, wherein the aqueous phase of the water-in-oil emulsion represents from 30 to 60% by weight of the total weight of the composition.

10. The composition according to claim 1, wherein the aqueous phase of the water-in-oil emulsion includes at least one additional polyol selected from the group consisting of:
glycols and homopolymers of glycols;
glycerol;
monosaccharides;
sorbitol;
disaccharides;
and mixtures thereof.

11. The composition according to claim 10, wherein the additional polyol is sucrose.

12. The composition according to claim 10, wherein:
glycol is selected from the group consisting of propylene glycol, dipropylene glycol and butylene glycol;
homopolymer of glycols is selected from the group consisting of poly(ethylene glycol)s and poly(propylene glycol)s;
monosaccharide is selected from the group consisting of glucose and fructose; and
disaccharide is sucrose.

13. The composition according to claim 1, wherein the polyol amount is between 25 and 35% weight by weight of the composition.

14. The composition according to claim 1, wherein it comprises at least one volatile oil in an amount between 5 and 8% weight by weight of the composition.

15. The composition according to claim 1, wherein the ratio of second to first copolymer is from 1/2 to 5/1.

16. The composition according to claim 1, wherein the ratio of second to first copolymer is from 1/1 to 2/1.

17. The composition according to claim 1, wherein the amount of first copolymer is from 0.5 to 5% by weight of the total weight of the composition.

18. The composition according to claim 1, wherein the non volatile hydrocarbon oil is selected from the group consisting of hydrogenated polydecene, hydrogenated polyisobutene, isopropyl palmitate, isononyl isononanoate and C12-C15 alkyl benzoate.

19. A cosmetic method for caring for or making up the lips, the eyebrows or skin, comprising topically applying, to the lips, the eyebrows or skin, the composition according to claim 1.

* * * * *